United States Patent [19]
Reis

[11] Patent Number: 5,593,407
[45] Date of Patent: Jan. 14, 1997

[54] INTERNAL ILIO-LUMBAR FIXATOR

[76] Inventor: Nicolas D. Reis, 11A Hague Street, Dania (PODB 55560) 34 980 Haifa, Israel

[21] Appl. No.: 211,913

[22] PCT Filed: Oct. 26, 1992

[86] PCT No.: PCT/GB92/01957

§ 371 Date: Oct. 13, 1994

§ 102(e) Date: Oct. 13, 1994

[87] PCT Pub. No.: WO93/07823

PCT Pub. Date: Apr. 29, 1993

[30] Foreign Application Priority Data

Oct. 26, 1991 [GB] United Kingdom ............... 9122753

[51] Int. Cl.⁶ .................................................. A61B 17/70
[52] U.S. Cl. .................. 606/61; 606/69; 606/73
[58] Field of Search ............................ 606/61, 69, 60, 606/70, 71, 72, 73; 623/17

[56] References Cited

U.S. PATENT DOCUMENTS 3,242,922  3/1966  Thomas .
4,773,402  9/1988  Asher et al. .
4,887,595  12/1989  Heinig et al. ........................ 606/61

FOREIGN PATENT DOCUMENTS 392927   10/1990  European Pat. Off. .
2631540  11/1989  France .
2178323  2/1987   United Kingdom .

*Primary Examiner*—Guy V. Tucker
*Attorney, Agent, or Firm*—Trexler, Bushnell, Giangiorgi & Blackstone, Ltd.

[57] ABSTRACT

Indirect lumbo-sacral fixation makes use of intact powerful ligaments joining the ilium to the sacrum by providing internal ilio-lumbar fixation in which tulip type pedicle screws (30) are screwed into the pedicles (46,48) at one side of the lowest lumbar vertebrae (47, 49) and are rigidly connected to a pelvic plate (31) secured by bone screws (52) to the posterior face of the adjacent ilium (51), the connection comprising a bent rod (32) having a knurled (or splined) spinal portion (33) secured in the pedicle screws by grub-screws (37) and locking screws (38) and having a non-circular male pelvic portion (35) fitting a mating female hole (40) and secured therein by a locking screw (41). Alternatively, the connection can include a universal joint between the pelvic portion of the bent rod and the pelvic plate, with three mutually perpendicular lockable pivotal connections.

17 Claims, 4 Drawing Sheets

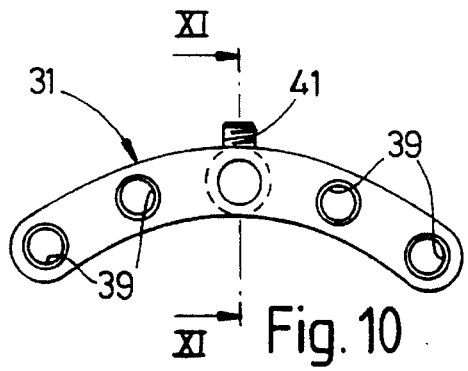
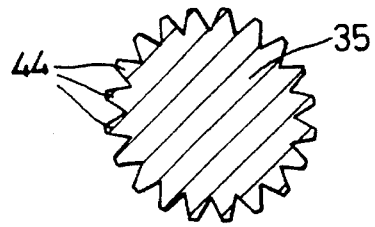
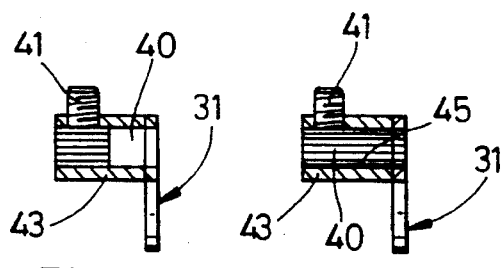
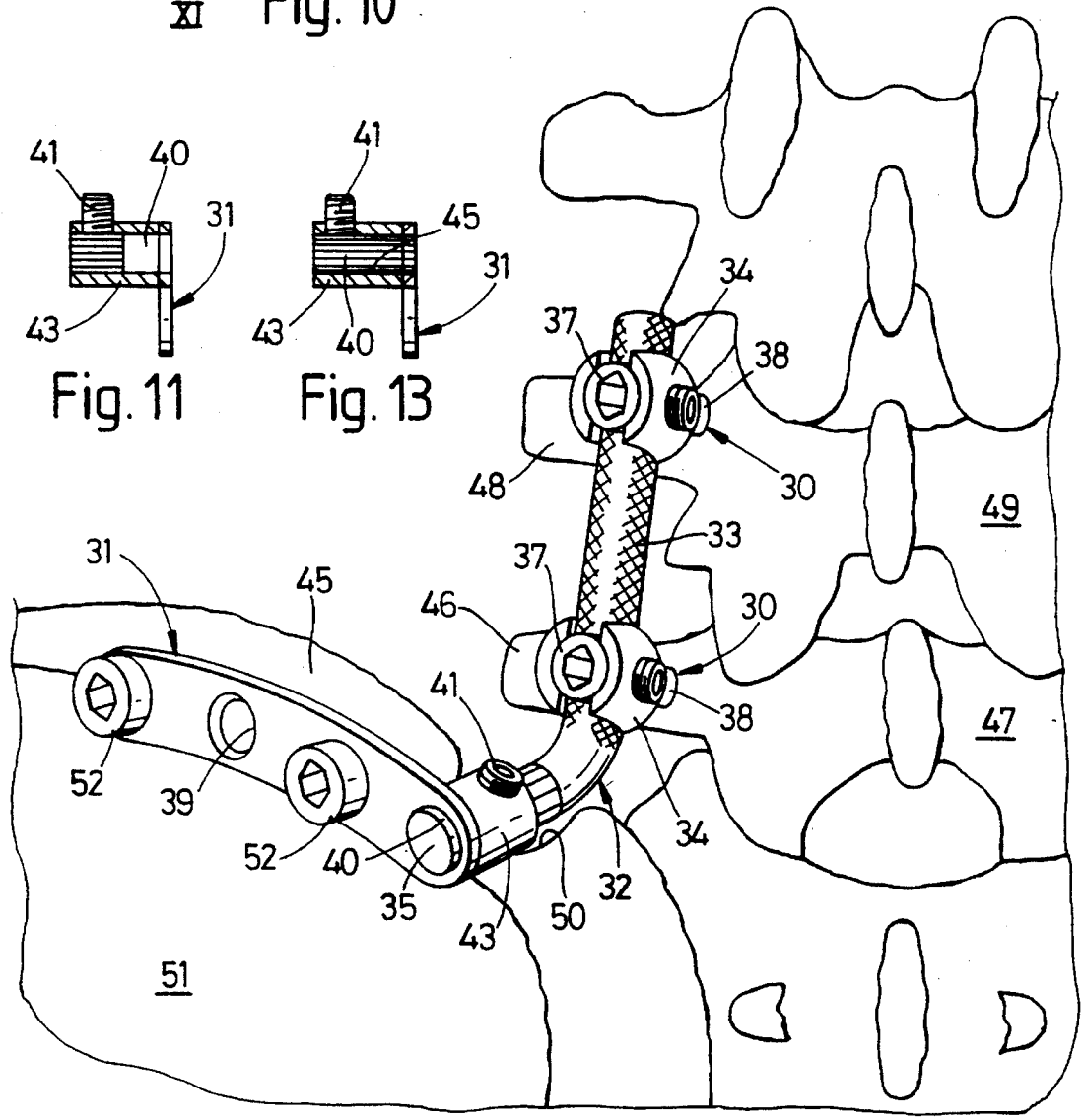

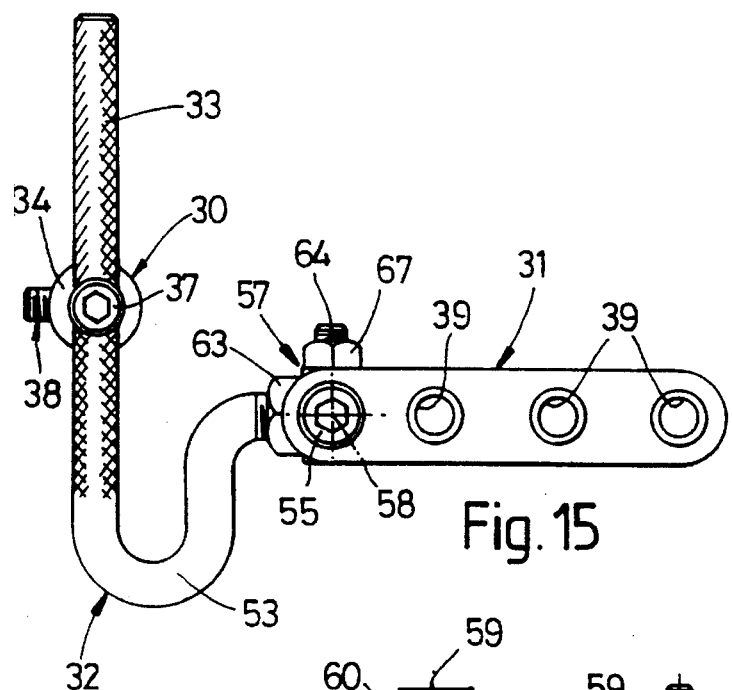
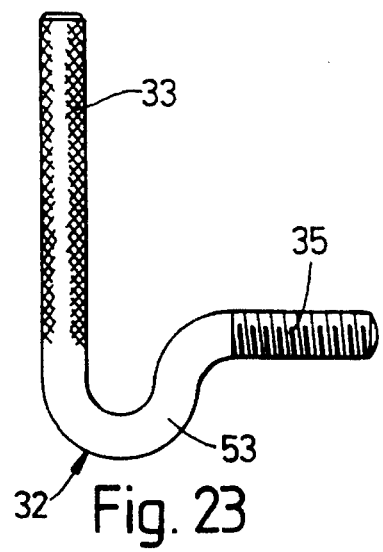
Fig. 15
Fig. 23
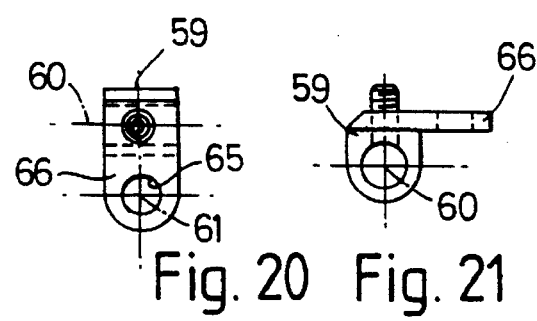
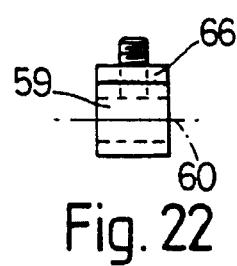
Fig. 20    Fig. 21    Fig. 22
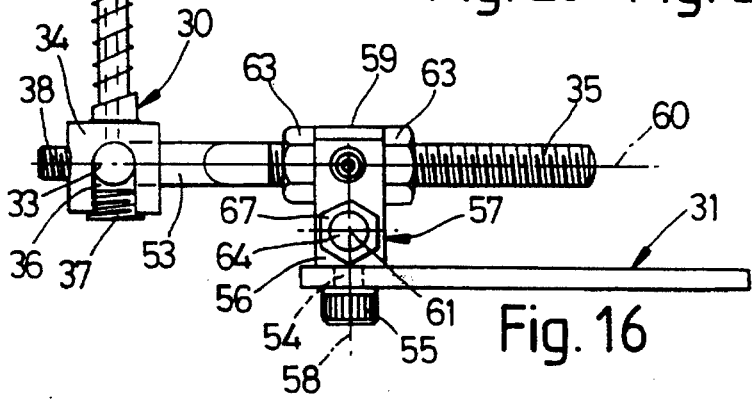
Fig. 16
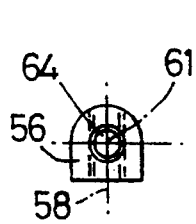
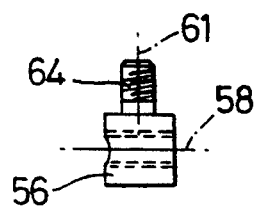
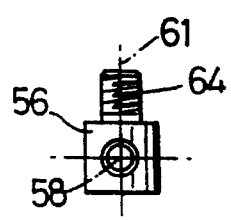
Fig. 17    Fig. 18    Fig. 19

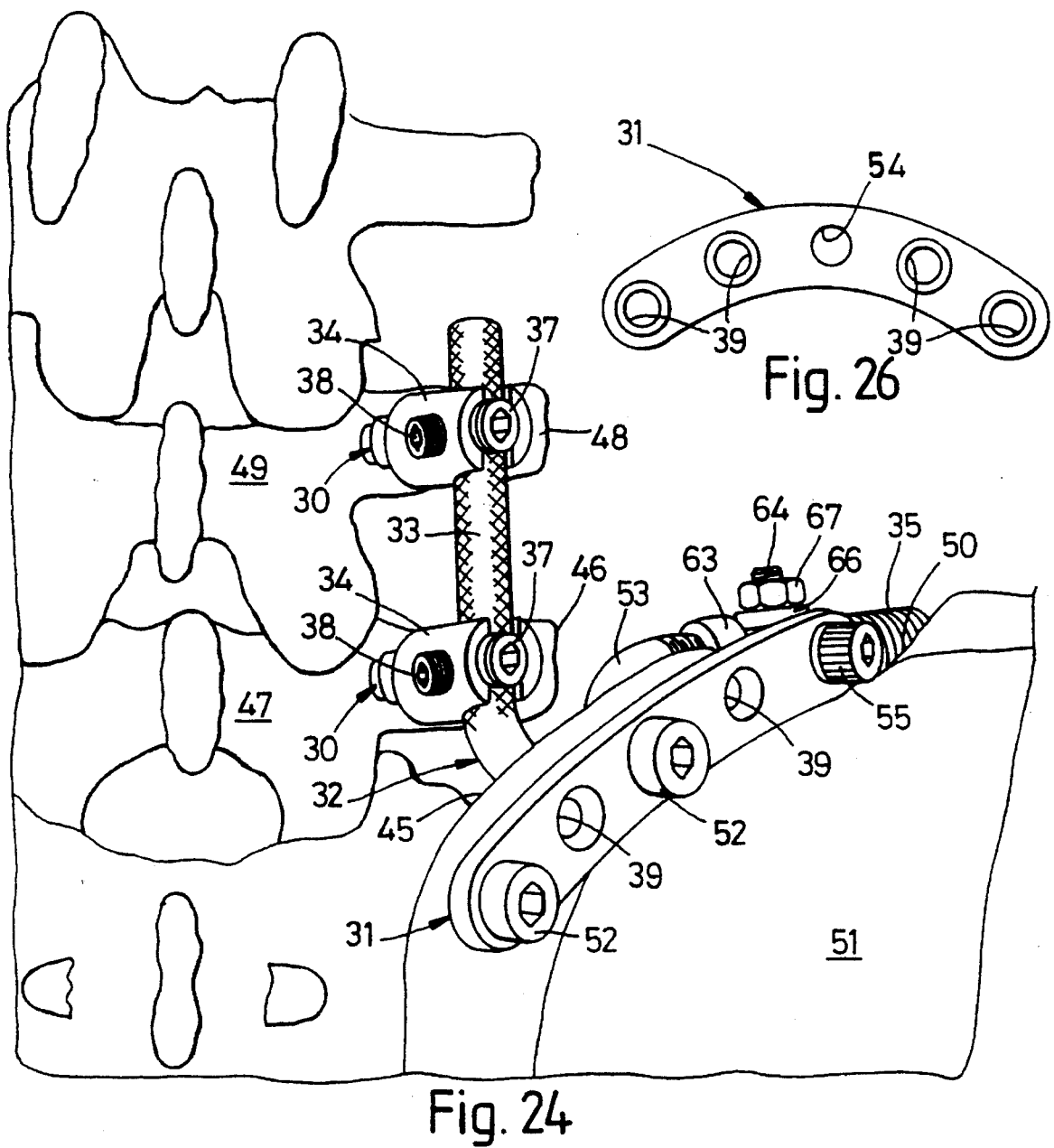
Fig. 26
Fig. 24
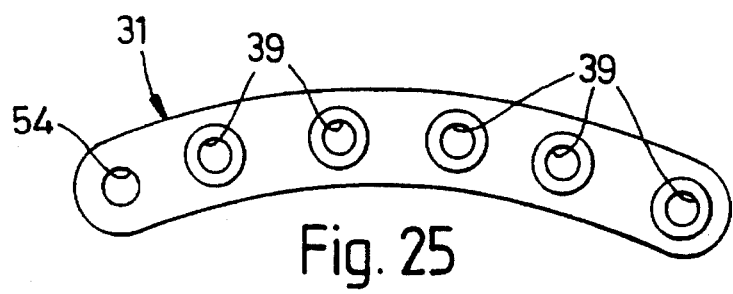
Fig. 25

INTERNAL ILIO-LUMBAR FIXATOR

This is a 35 U.S.C. 371 application based on PCT/GB92/01957, filed Oct. 26, 1992.

FIELD OF THE INVENTION

This invention relates to internal ilio-lumbar fixation. Fixing of the ilium to the lower lumbar vertebrae may be required for (a) various diseases of the vertebral column; or (b) fractures and/or dislocations of the sacro-iliac joint region resulting in an unstable hemi-pelvis; this fixation being necessary to indirectly immobilise the lumbo-sacral segment whilst fusion is taking place after a bone graft, to stabilise an unstable lumbo-sacral spine due to fracture or disease, to reduce and correct a deformity of the spine, or to reduce and immobilise a sacro-iliac region fracture or dislocation until healing has taken place.

BACKGROUND OF THE INVENTION

In the past, ilio-lumbar fixation has been attempted by (a) the Magerl method in which external fixator pins are applied from behind to transfix the posterior mass of each ilium and other pins transfix the pedicles of a lumbar vertebrae, these fixators then being connected by an external frame, but this method has a very limited application and has not been generally adopted; (b) the Galveston method in which rods affixed to the spine by various means are passed through or into the posterior iliac mass from medial to lateral, being used mainly for very extensive corrections of spinal deformity when there is a need to fix the lumbo-sacral segment, affording limited stability to this segment in the saggital plane but only very poor stability in the coronal plane and rotation.

Many methods also exist that attempt to achieve direct lumbo-sacral fixation, i.e. between the lowest lumbar vertebrae and the sacrum, all of which use some form of screw fixation into the sacrum itself, but there is a danger of damaging nerves in or exiting from the sacrum, and the poor mechanical quality of sacral bone makes the strength of the screw fixation to the sacrum unpredictable.

SUMMARY OF THE INVENTION

The present invention achieves an indirect lumbo-sacral fixation making use of intact powerful ligaments joining the ilium to the sacrum.

According to one aspect of the present invention, for use when there is no structural disruption and the sacro-iliac ligaments are intact, an internal ilio-lumbar fixation comprises at least one pedicle screw of the tulip type, a pelvic plate (preferably curved to match an iliac crest formation), and a bent rod having a spinal portion for engagement in the bifurcated head of the pedicle screw and a pelvic portion for engagement with the pelvic plate; in which combination:

the pedicle screw has a washer within its bifurcated head to embrace the spinal portion of the bent rod and to be pressed into firm engagement therewith by the usual grubscrew screwing into the bifurcated head, and at least one additional locking screw in a screwthreaded hole through one side of the head to engage the spinal portion of the bent rod;

the pelvic plate has at least two holes for bone screws, another hole having a non-circular female cross-section, and a locking screw in a screwthreaded hole opening into at least one side of the female hole;

and the bent rod having a mating male cross-section along a major part of its pelvic portion affording a close sliding fit in the female hole in the pelvic plate.

In use, the bifurcated tulip type pedicle screw is screwed into a hole in one pedicle of the lowest lumbar vertebra, the spinal portion of the bent rod is fitted into the bifurcated head of the pedicle screw with the pelvic portion projecting through a notch in the adjacent ilium and projecting up to or beyond the posterior face of that ilium, the pelvic plate is engaged with the pelvic portion of the bent rod by fitting of the female hole on to the part of the bent rod having a mating male cross-section and, with the pelvic plate extending over the posterior face of the ilium, the pelvic plate is secured to the ilium by bone screws. The washer is fitted into the bifurcated head of the pedicle screw and pressed into firm engagement with the spinal portion of the bent rod by screwing the usual grubscrew into the bifurcated head, and the locking screw in the pelvic plate and the additional locking screw in the pedicle screw are screwed in tight against the pelvic portion and the spinal portion respectively of the bent rod.

The angle between the spinal portion and the pelvic portion of the bent rod can be adjusted by the surgeon, if necessary, for example to produce spinal lordosis and/or to fit the pelvic portion easily into the female hole in the pelvic plate.

The final fixation of the rod at the spinal and pelvic ends dan be done in distraction, compression lordosis, kyphosis or in situ as required by various indications.

The spinal portion of the bent rod may be knurled or splined and the face of the washer for engagement therewith provided with a complementary formation.

The spinal portion of the bent rod is preferably long enough to enable it to fit within a second pedicle screw of the tulip type screwed into the corresponding pedicle of the next vertebra.

The pelvic plate preferably has a thicker portion in which is provided the female hole and the locking screw hole, and the female hole may be provided at one end of the pelvic plate, or it may be provided intermediate the ends of the pelvic plate, to allow for selective variation in the disposition of the pelvic plate on the posterior face of the ilium.

The female hole may have a polygonal cross-section which is preferably twelve-sided thus providing 30° increments of adjustment in the position of the pelvic plate in relation to the bent rod, the pelvic portion of which has a corresponding polygonal cross-section. Alternatively, the pelvic portion of the bent rod may be splined e.g., with twenty splines providing 18° increments of adjustment, and the female hole is provided with at least one mating rib.

When using the device for sacro-iliac region fracture dislocations it is applied only on the side of the injury. In the surgery for spinal diseases or injuries the device will be usually applied bilaterally. Further stability may be obtained by adding a metal bridging segment to connect the right and left rods.

According to another aspect of the present invention, for use when reduction of a pelvic fracture or other fracture or dislocation in the sacro-iliac area is required, an internal ilio-lumbar fixation comprises at least one pedicle screw of the bifurcated type, a pelvic plate (preferably curved to match an iliac crest formation), a bent rod having a spinal portion for engagement in the bifurcated head of the pedicle screw and a pelvic portion for connection to the pelvic plate, and two universal joint members between the spinal portion of the bent rod and the pelvic plate, in which combination:

the pedicle screw has a washer within its bifurcated head to embrace the spinal portion of the bent rod and to be pressed into firm engagement therewith by the usual grubscrew screwing into the bifurcated head, and at least one additional locking screw in a screwthreaded hole through one side of the head to engage the spinal portion of the bent rod;

the pelvic plate has at least two holes for bone screws and another hole for a screw forming a first lockable pivotal connection with one of the universal joint members;

the pelvic portion of the bent rod has a second lockable pivotal connection with the other universal joint member the axis of which is perpendicular to the first lockable pivotal connection;

and the universal joint members are joined together by a third lockable pivotal connection the axis of which is perpendicular to the first and second lockable pivotal connections respectively.

In use, the tulip pedicle screw is screwed into a hole in one pedicle of the lowest lumbar vertebra, the spinal portion of the bent rod is fitted into the bifurcated head of the pedicle screw, with the pelvic portion extending anteriorly alongside the adjacent ilium, the washer is fitted into the bifurcated head of the pedicle screw and pressed into firm engagement with the spinal portion of the bent rod by screwing the usual grubscrew into the bifurcated head, the additional locking screw in the pedicle screw is screwed in tight against the spinal portion of the bent rod, the pelvic plate is secured to the posterior face of the ilium by bone screws with the hole for the screw forming the first lockable pivotal connection in register with a notch in the ilium, which notch enables the universal joint members to be fitted between the pelvic plate and the pelvic portion of the bent rod, and all three lockable pivotal connections are tightened up to secure the ilium (or the part of it to which the pelvic plate is secured) in correct relative disposition to the lumbar vertebra.

The spinal portion of the bent rod is preferably knurled or splined and the face of the washer for engagement therewith is preferably provided with a complementary formation.

The spinal portion of the bent rod is preferably long enough to enable it to fit within a second pedicle screw the bifurcated head type screwed into the corresponding pedicle of the next vertebra.

The second lockable pivotal connection may be formed by the pelvic portion of the bent rod being screwthreaded and fitting through a hole in its respective universal joint member, with a pair of nuts on the screwthreaded portion to bear against opposite faces of that joint member.

The third lockable pivotal connection may be formed by a screw extending from one of the universal joint members through a hole in a lug on the other universal joint member, and a nut screwing on to the screw; and the mutually facing faces of the one joint member and of the lug of the other joint member may be provided with radiating mating ribs and grooves to afford positive locking of the third pivotal connection.

The hole for a screw forming the first lockable pivotal connection may be provided at one end of the pelvic plate, or it may be provided intermediate the ends of the pelvic plate, to allow for selective variation in the disposition of the pelvic plate on the posterior face of the ilium.

Preferably the pedicle screws are cannulated so that they can be introduced over a guide wire. In practice a surgeon, in order to establish the exact path for the introduction of the screw, will make a portal into the appropriate vertebrae, by means of an awl (or the like) and then introduce a guide wire passing through the centre of the pedicle into the body of the vertebrae. The position of the guide wire is then checked by means of an imaging technique, and once the surgeon is satisfied that said wire lies in the correct position the pedicle screw is driven over the wire. It can be seen that the provision of cannulated pedicle screws, thus enabling the screw to be positioned by means of a guide wire, considerably reduces the likelihood of inadvertently piercing the spinal canal with the screw, so avoiding causing damage to the neural structures therewithin.

BRIEF DESCRIPTION OF THE DRAWINGS

Embodiments of both aspects of the invention will now be described, by way of example only, with reference to the accompanying drawings in which:

FIG. 10 is an elevation of a curved pelvic plate;

FIG. 11 is a section from the line XI—XI in FIG. 10 with a female hole formation corresponding to the male section shown in FIG. 9;

FIG. 12 corresponds to FIG. 9 but shows an alternative male cross-section;

FIG. 13 corresponds to FIG. 11 but shows a single rib in the female hole to mate with the male cross-section of FIG. 12;

FIG. 14 is a fragmentary perspective view showing a preferred embodiment in accordance with the first aspect of the invention in operative position.

FIG. 15 is an elevation of a basic embodiment in accordance with the second aspect of the invention;

FIG. 16 is a plan view of the embodiment of FIG. 15;

FIG. 17 is a plan view of a first universal joint member;

FIG. 18 is an elevation from the left hand side of FIG. 17;

FIG. 19 is an elevation from the left-hand side of FIG. 18;

FIG. 20 corresponds to a part of FIG. 16 showing detail of the other universal joint member;

FIG. 21 is an elevation from the left-hand side of FIG. 20;

FIG. 22 is an elevation from the left-hand side of FIG. 21;

FIG. 23 is an elevation of a bent rod usable in place of the bent rod shown in FIGS. 15 and 16;

FIG. 24 is a fragmentary perspective view showing a preferred embodiment in accordance with the second aspect of the invention in operative position;

FIG. 25 is an elevation of a curved pelvic plate of opposite hand to the pelvic plate included in FIG. 24, and also having more bone screw holes; and FIG. 26 is an elevation of a pelvic plate having a sharper curvature than those in FIGS. 24 and 25, and also having its hole for a screw forming the first lockable pivotal connection intermediate its ends.

DESCRIPTION OF THE INVENTION

Figure 2:
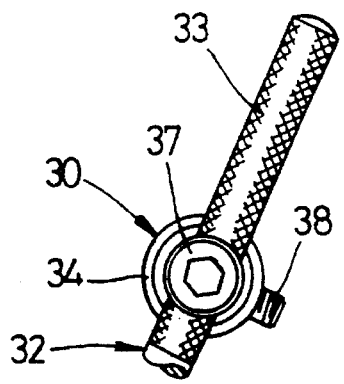
FIG. 2 is a fragmentary elevation in the direction of the arrow II in FIG. 1.
Figure 9:
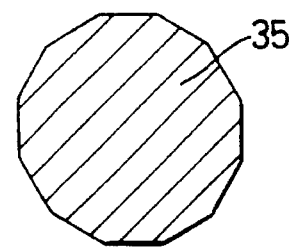
FIG. 9 is a greatly enlarged cross-section on the line IX—IX in FIG. 1.
Figure 1:
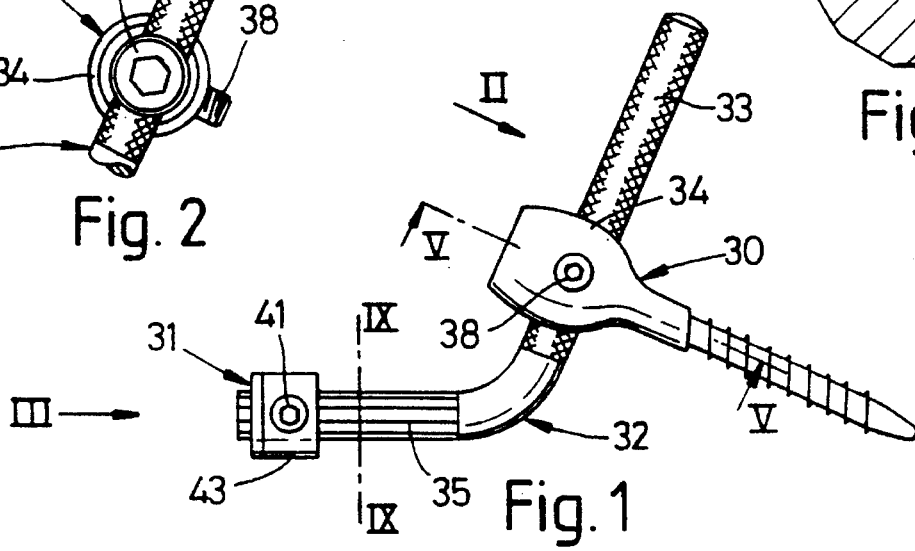
FIG. 1 is an elevation of a basic embodiment in accordance with the first aspect of the invention.

The internal ilio-lumbar fixation shown in FIG. 1 comprises a pedicle screw 30 of the tulip type, a pelvic plate 31, and a bent rod 32 having a spinal portion 33 for engagement in the bifurcated head 34 of the pedicle screw and a pelvic portion 35 for engagement with the pelvic plate; in which combination:

the pedicle screw 30 has a washer 36 (see FIGS. 5 to 8) within its bifurcated head 34 to embrace the spinal portion 33 of the bent rod 32 and To be pressed into firm engagement therewith by the usual grubscrew 37 (see also FIG. 2) screwing into the bifurcated head, and an additional locking screw 38 in a screwthreaded hole through one side of the head 34 to engage the spinal portion of the bent rod;

the pelvic plate 31 has three holes 39 for bone screws (not shown, but see FIG. 14), another hole 40 having a polygonal female cross-section with twelve sides (see also FIGS. 3 and 4), and a locking screw 41 in a screwthreaded hole opening into one side of the female hole 40;

and the bent rod 32 having a mating male cross-section (see also FIG. 9) along a major part of its pelvic portion 35 affording a close sliding fit in the female hole in the pelvic plate.

Figure 7:
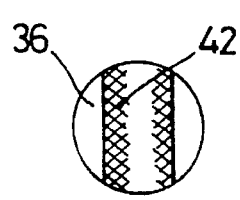
FIG. 7 is an underneath view of the washer.
Figure 8:
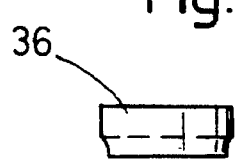
FIG. 8 is a side elevation of the washer perpendicular to its elevation in FIG. 5.

The spinal portion 33 of the bent rod 32 is knurled (but may, alternatively, be splined) and the face of the washer 36 for engagement therewith is provided with a complementary formation 42 (see particularly FIG. 7).

The pelvic plate 31 has a thicker portion (or boss) 43 (see also FIGS. 11 and 13) in which is provided the female hole 40 and the hole for the locking screw 41, and the female hole may be provided at one-end of the pelvic plate (as in FIGS. 3 and 4 or FIG. 14) or it may be provided intermediate the ends of the pelvic plate (as shown in FIG. 10).

FIG. 12 shows an alternative male cross-section for the pelvic portion 35 of the bent rod 32 having twenty splines 44, and the alternative female hole 40 is shown in FIG. 13 with a single longitudinal rib 45 for engagement in any one of the grooves between adjacent splines 44.

Figure 3:
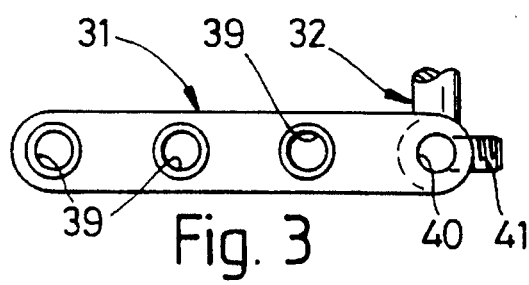
FIG. 3 is a fragmentary elevation in the direction of the arrow III in FIG. 1.
Figure 5:
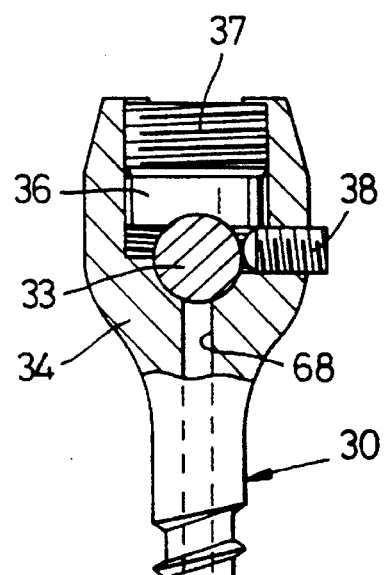
FIG. 5 is an enlarged fragmentary view partly in section on the line V—V in FIG. 1.
Figure 4:
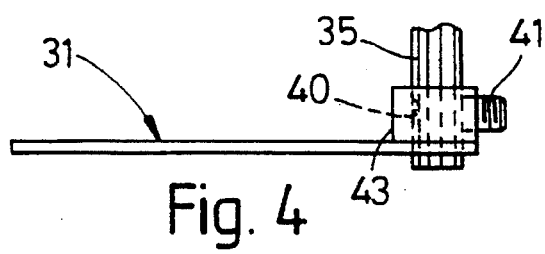
FIG. 4 is a plan view of FIG. 3.
Figure 6:
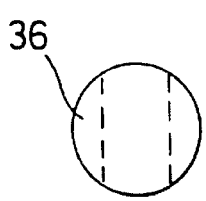
FIG. 6 is a plan view of the washer visible in FIG. 5.

Although the pelvic plate 31 in FIGS. 1, 3 and 4 is straight, it is preferable rouse curved pelvic plates such as are shown in FIGS. 10, 11, 13 and FIG. 14, with a curvature to match an iliac crest formation, such as the formation 45 shown in FIG. 14 which will now be referred to in describing use of an embodiment of the first aspect of the invention.

The spinal portion 33 of the bent rod is long enough to enable it to span from one pedicle 46 of the lowest lumbar vertebra 47 to the corresponding pedicle 48 of the next vertebra 49.

Two bifurcated tulip type pedicle screws 30 are screwed one into a hole in each of the pedicles 46, 48, the spinal portion 33 of the bent rod 32 is fitted into the bifurcated heads 34 with the pelvic portion 35 of the bent rod projecting through a notch 50 in the adjacent ilium 51, the pelvic plate 31 is engaged with the pelvic portion of the bent rod by fitting the female hole 40 on to the mating male part, which with the twelve sides affords increments of angular adjustment of 30° each (or, with the twenty splines 44 affords increments of 18° each) and, with the pelvic plate extending over the posterior face of the ilium, the pelvic plate is secured to the ilium by bone screws 52.

The washers 36 are fitted into the bifurcated heads 34 of the pedicle screws 30 and pressed into firm engagement with the spinal portion 33 of the bent rod 32 by screwing in the grubscrews 37, and the locking screw 41 in the pelvic plate 31 and the additional locking screws 38 in the pedicle screws are screwed in tight against the pelvic portion and the spinal portion respectively of the bent rod.

In addition to being able to adjust the angle between the spinal portion 33 and the pelvic portion 35 of the bent rod 32, the surgeon can select a curved pelvic plate 31 to match a particular part of the iliac crest formation 45 to one side or the other, or both sides of the notch 50 in the ilium. Final fixation of the rod 32 at the spinal and pelvic ends can be done in distraction, compression lordosis, kyphosis or in situ as required for any particular indication.

The internal ilio-lumbar fixation shown in FIGS. 15 and 16 (with details shown in FIGS. 17 to 22) comprises a pedicle screw 30, a pelvic plate 31 and a bent rod 32 somewhat similar to those in the previous embodiments except for a differently shaped bend 53 in the bent rod 32 and a plain cylindrical hole 54 in the pelvic plate 31 in place of the non-circular hole 40, for a screw 55 which forms a first lockable pivotal connection with a first member 56 of a universal joint 57 having an axis 58;

the pelvic portion 35 of the bent rod has a second lockable pivotal connection with a second universal joint member 59 the axis 60 of which is perpendicular to the first lockable pivotal connection;

and the universal joint members 56, 59 are joined together by a third lockable pivotal connection the axis 61 of which is perpendicular to the first and second lockable pivotal connections respectively.

The second lockable pivotal connection is formed by the pelvic portion 35 of the bent rod being screwthreaded, and fitting through a hole 62 in the second universal joint member 59, with a pair of nuts 63 on the screwthreaded portion to bear against opposite faces of that joint member.

The third lockable pivotal connection is formed by a screw 64 extending from the first universal joint member 56 through a hole 65 in a lug 66 on the second universal joint member 59, and a nut 67 screwing on to the screw.

In FIGS. 25 and 26, which show two preferred curved pelvic plates, the hole 54 for the screw 55 forming the first lockable pivotal connection is provided, respectively, at one end of the pelvic plate and intermediate The ends of the pelvic plate. This allows for selective variation of the type and disposition of pelvic plates on the posterior face of the ilium 51 and matching the iliac crest formation 45 as again shown in FIG. 24, in which the pelvic plate is of opposite hand to that shown in FIG. 25 (which also has more holes).

Even the smaller bent rod 32 shown in FIG. 23 has a spinal portion 33 long enough to enable it to span from one pedicle 46 of The lowest lumbar vertebra 47 to the corresponding pedicle 48 of the next vertebra 49, as in the preferred embodiment of the second aspect of the invention shown in use in FIG. 24.

Two Tulip pedicle screws 30 are screwed into respective holes in the pedicles 46, 48, the spinal portion 33 of the bent rod 32 is fitted into the bifurcated heads 34, with the pelvic portion 35 of the bent rod extending anteriorly alongside the adjacent ilium 51, washers 36 are fitted into the bifurcated heads and pressed into firm engagement with the spinal portion of the bent rod by screwing grubscrews 37 into The bifurcated heads, and the additional locking screws 38 in the pedicle screws 30 are screwed in tight against the spinal portion of the bent rod.

The pelvic plate 31 is secured to the posterior face of the ilium 51 by bone screws 39 with the hole 54 for the screw 55 in register with a notch 50 in the iliac crest formation 45, which notch enables the universal joint members 56, 59 to be fitted between the pelvic plate 31 and the pelvic portion 35 of the bent rod 32, and all three lockable pivotal connections are tightened up to secure the ilium (or the part of it to which the pelvic plate is secured) in correct relative disposition to the lumbar vertebra.

The pedicle screws 30 have cannulae 68 (see FIGS. 5 and 16) so that they can be introduced over a guide wire (not shown).

I claim:

1. An internal ilio-lumbar fixator comprising at least one pedicle screw with a bifurcated head, a pelvic plate and a bent rod having a spinal portion for engagement in the bifurcated head of the pedicle screw and a pelvic portion for engagement with the pelvic plate; in which combination:

the pedicle screw has a washer within said bifurcated head to embrace the spinal portion of the bent rod and to be pressed into firm engagement therewith by a grubscrew secured into the bifurcated head, and at least one additional locking screw in a screwthreaded hole through one side of the bifurcated head to engage the spinal portion of the bent rod;

the pelvic plate has at least two holes for bone screws, another hole having a non-circular female cross-section, and a locking screw in a screwthreaded hole opening into at least one side of the female hole;

and the bent rod having a mating male cross-section along a major part of its pelvic portion affording a close sliding fit in the female hole in the pelvic plate.

2. A fixator as in claim 1, wherein the pelvic plate has a thicker portion in which is provided the female hole and the screwthreaded hole.

3. A fixator as in claim 1 or claim 2, wherein the female hole is provided at an end formed on the pelvic plate.

4. A fixator as in claim 1 or claim 2, wherein the female hole is provided intermediate two ends formed on the pelvic plate.

5. A fixator as in claim 1 or claim 2, wherein the female hole has a polygonal cross-section.

6. A fixator as in claim 5, wherein the polygonal cross-section is twelve-sided.

7. A fixator as in claim 1, wherein the pelvic portion of the bent rod is splined, and the female hole is provided with at least one mating rib.

8. A fixator as in claim 7, wherein there are twenty splines.

9. A fixator as in claim 1, wherein the pelvic plate is curved to match an iliac crest formation.

10. A fixator as in claim 1, wherein the spinal portion of the bent rod is knurled or splined and the face of the washer for engagement therewith provided with a complementary formation.

11. A fixator as in claim 1, wherein the spinal portion of the bent rod is long enough to enable it to fit within a second pedicle screw of the tulip type screwed into the corresponding pedicle of the next vertebra.

12. A fixator as in claim 1, wherein the pedicle screws are cannulated so that they can be introduced over a guide wire.

13. An internal ilio-lumbar fixation comprising at least one pedicle screw with a bifurcated type, a pelvic plate, a bent rod having a spinal portion for engagement in the bifurcated head of the pedicle screw and a pelvic portion for connection to the pelvic plate, and two universal joint members between the pelvic portion of the bent rod and the pelvic plate, in which combination:

the pedicle screw has a washer within said bifurcated head to embrace the spinal portion of the bent rod and to be pressed into firm engagement therewith by a grubscrew secured into the bifurcated head, and at least one additional locking screw in a screwthreaded hole through one side of the bifurcated head to engage the spinal portion of the bent rod;

the pelvic plate has at least two holes for bone screws and another hole for a screw forming a first lockable pivotal connection with one of the universal joint members;

the pelvic portion of the bent rod has a second lockable pivotal connection with the other universal joint member the axis of which is perpendicular to the first lockable pivotal connection;

and the universal joint members are joined together by a third lockable pivotal connection the axis of which is perpendicular to the first and second lockable pivotal connections respectively.

14. A fixator as in claim 13, wherein the second lockable pivotal connection is formed by the pelvic portion of the bent rod being screwthreaded and fitting through a hole in its respective universal joint member, with a pair of nuts on the screwthreaded portion to bear against opposite faces of the respective universal joint member.

15. A fixator as in claim 13, wherein the third lockable pivotal connection is formed by a screw extending from one of the universal joint members through a hole in a lug on the other universal joint member, and a nut screwing on to the screw.

16. A fixator as in any one of claims 13 to 15, wherein the hole for a screw forming the first lockable pivotal connection is provided at an end formed on the pelvic plate.

17. A fixator as in any one of claims 13 to 15, wherein the hole for a screw forming the first lockable pivotal connection is provided intermediate two ends formed on the pelvic plate.

* * * * *